United States Patent [19]
Cutting et al.

[11] Patent Number: 5,407,796
[45] Date of Patent: Apr. 18, 1995

[54] CYSTIC FIBROSIS MUTATION CLUSTER

[75] Inventors: Garry R. Cutting, Towson; Stylianos E. Antonarakis, Lutherville; Haig H. Kazazian, Jr., Baltimore, all of Md.

[73] Assignee: The Johns Hopkins University, Baltimore, Md.

[21] Appl. No.: 637,621

[22] Filed: Jan. 4, 1991

[51] Int. Cl.$^6$ .................... C07H 21/00; C12N 15/10; C12P 19/34; C12Q 1/68
[52] U.S. Cl. ...................................... 435/6; 435/91.2; 536/23.2; 536/24.31; 935/77; 935/78
[58] Field of Search ............................ 435/6, 91, 91.2; 436/94; 536/27, 23.2, 24.31; 935/77, 78

[56] References Cited
PUBLICATIONS

Kerem, et al., Science, vol. 245, pp. 1073–1080, 1989.
Riordan, et al., Science, vol. 245, pp. 1066–1073, 1989.
Rommens, et al., Science, vol. 245, pp. 1059–1065, 1989.
Sheffield, et al., Proc. Natl. Acad. Sci. USA, vol. 86, pp. 232–236, 1989.
Orita, M. et al, "Rapid & Sensitive Detection of Point Mutations & DNA Polymorphisms Using PCR," Genomics 5:874–879 (1989).
Cuppens, H. et al. "A Child Homozygous for a Stop Codon in Exon 11," J. Med. Genet. 27(11):717–719 (1990).
Cutting, G. R. et al. "A Cluster of Cystic Fibrosis Mutations in the First Nucleotide–Binding Fold of the Cystic Fibrosis Conductance Regulator Protein," Nature 346:366–369. (1990).
Kerem, B. *PNAS* 87:8447–8451 (1990).

*Primary Examiner*—Robert A. Wax
*Assistant Examiner*—Dian C. Jacobson
*Attorney, Agent, or Firm*—Banner, Birch, McKie & Beckett

[57] ABSTRACT

Four mutations have been found clustered in exon 11 of the CFTR (cystic fibrosis transmembrane conductance regulator) gene. These mutations occur within a set of amino acids highly conserved among ATP-dependent transport proteins. Humans can be tested to determine whether they carry one of these mutations using a number of methods and/or probes taught herein. Specifically the mutations include: $Asn_{549}$, $Asp_{551}$, $Stop_{553}$, and $Thr_{559}$.

33 Claims, 2 Drawing Sheets

CYSTIC FIBROSIS MUTATION CLUSTER

This invention was made using U.S. government funds awarded by the National Institutes of Health as DK 39635 and DK 34944. Therefore the government has certain rights in the invention.

BACKGROUND OF THE INVENTION

Cystic fibrosis (CF), the most common lethal autosomal genetic disorder in the Caucasian population, occurs approximately once in every 2500 live births (Boat, et al., *The Metabolic Basis of Inherited Disease*, eds. Shriver, et al., McGraw-Hill, New York (1989) pp. 2649-2680). A single locus for CF has been mapped to chromosome 7q31 by linkage analysis using DNA marker probes.

Several markers have been shown to have a high degree of linkage disequilibrium with the CF locus in Caucasians suggesting that one mutation of the CF gene predominates in this population (Estivill, et al., Nature, (1987), 326:840; Estivill, et al., Genomics, (1987), 1:257). DNA polymorphism haplotypes from phenotypically and racially diverse patient populations indicated that several additional mutations of the CF gene may exist in these groups (Ober, et al., Am. J. Hum. Genet., vol. 41, p. 1145, 1987; Estivill, et al., ibid., vol. 43, p. 23 (1988); Fujiwara, et al., ibid., vol. 44, p. 327, (1989); Kerem, et al., ibid. p. 827 and Cutting, et al., ibid., p. 307).

The gene responsible for CF has recently been identified (Rommens, et al., Science, vol. 245, p. 1059 (1989); Riordan, et al., ibid., p. 1066); it comprises 20 exons and encodes a protein of 1480 amine acids called the CF Transmembrane Conductance Regulator (CFTR). Several regions are postulated to have functional importance in the CFTR protein, including two areas for ATP binding, termed Nucleotide Binding Folds (NBF), a Regulatory (R) region that has multiple potential sites for phosphorylation by protein kinases A and C, and two hydrophobic regions believed to interact with cell membranes.

One mutation has been identified in the CF gene which leads to the omission of phenylalanine residue 508 within the first putative NBF domain, indicating that this region is functionally important. This mutation, termed $\Delta F_{508}$, accounts for about 70% of the CF chromosomes in Caucasian patients and was highly associated with the predominant haplotype found on chromosomes of Caucasian CF patients (Kerem, et al., Science, vol. 245, p. 1073 (1989); Lemna, et al., New Engl. J. Med., vol. 322, p. 291 (1990)); the haplotypes associated with Caucasian CF chromosomes without $\Delta F508$ are less common, confirming predictions that allelic heterogeneity exists in CF (Ober, et al., Am. J. Hum. Genet., vol. 41, p. 1145, 1987; Estivill, et al., ibid., vol. 43, p. 23 (1988); Fujiwara, et al., ibid., vol. 44, p. 327, (1989); Kerem, et al., ibid. p. 827 and Cutting, et al., ibid., p. 307; Kerem, et al., Science, vol. 245, p. 1073 (19S9)).

There is a need in the art of genetic screening for knowledge of other mutant alleles of CFTR which are present on the other 30% of CF chromosomes in Caucasian CF patients, as well as other alleles found in other racial groups. Knowledge of such alleles can be used to design probes for screening, as well as to devise other screening methods. The more complete the set of probes available for CF mutant alleles, the more accurate diagnoses can be made.

SUMMARY OF THE INVENTION

It is an object of the invention to provide nucleic acid probes for detecting mutant CFTR alleles other than $\Delta F_{508}$.

It is another object of the invention to provide methods of testing a DNA sample of a human for the presence of mutant alleles of the CFTR gene other than $\Delta F_{508}$.

These and other objects of the invention are provided by one or more of the embodiments described below. In one embodiment a nucleic acid probe is provided which is complementary to a mutant allele of the CFTR gene selected from the group consisting of: $Asn_{549}$, $Asp_{551}$, $Stop_{553}$, and $Thr_{559}$.

In another embodiment of the invention a method is provided for testing a DNA sample of a human to determine if the human is a carrier of Cystic Fibrosis or if the human is affected with Cystic Fibrosis, comprising:
  providing a DNA sample from a human;
  testing the sample for the presence of a mutation in exon 11 of the CFTR gene of the human, the presence of the mutation indicating that the human is a carrier of Cystic Fibrosis or is affected with Cystic Fibrosis.

These and other embodiments are described with more particularity below. They provide the art with the knowledge of four hitherto unknown mutant alleles which are present in human populations and which can lead to cystic fibrosis if they are not present in a heterozygous configuration with a wild-type allele. In the case of a heterozygote, the individual is a "carrier", but will not be affected himself. If the mutant alleles are present with other mutant alleles, then the individual will be affected with the cystic fibrosis disease. These newly discovered alleles allow for genetic screening to provide more accurate diagnoses. Previously, without knowledge of these alleles, individuals carrying these alleles would have been "false negatives", i.e., they would have appeared to carry a wild-type allele because they did not carry any of the known mutant alleles.

DETAILED DESCRIPTION

It is a finding of the present invention that four mutations which cause cystic fibrosis (if present in an individual who lacks a wild-type allele) are clustered in a region of exon 11 of the CFTR gene consisting of nucleotides 1778-1807. (The numbering of nucleotides used herein follows the numbering of Riordan et al., Science vol. 245, p.1066, 1989.) See SEQ ID NO: 1. Thus exon 11 comprises a "hotspot" for CF mutations. The corresponding region of the protein is contained within the postulated first (N-terminal) nucleotide binding fold domain, a region which is highly conserved among a large number of homologous proteins. Each of the four mutations is a transversion, three causing amino acid substitutions and one producing a termination codon.

One mutation. $G_{1784}$ to A, was found in 4% of the Caucasian CF chromosomes studied. (The allele which carries this mutation is termed the Asp551 allele herein.) The stop codon mutation (caused by a thymidine at nucleotide number 1789 leading to a translational stop after 552 amino acid residues,) was found in 5% of the American Black CF chromosomes studied. The other two mutations are rare in the American Black patients. These are both G to A mutations located at nucleotides 1778 and 1807, and lead to an asparagine and threonine residue, respectively. See Table 2.

The possibility that the three missense mutations are normal variants of the CFTR gene was ruled out by sequencing or restriction digestion of non-CF chromosomes with the same haplotype as that associated with each particular mutation. As shown in Table 3, none of the non-CF chromosomes of the same haplotype carried the mutations described herein. Therefore the missense mutations are not normal variants of the gene.

The $Asp_{551}$ allele taught herein is to date the second most common CF mutation in Caucasian chromosomes. The mutation on the allele causes the substitution of glycine, a neutral amino acid, with aspartic acid, a polar amino acid. This charge change makes it unlikely that the allele codes for a normal polymorphic variant of the CFTR protein. In addition, even though the mutation occurs on 4% of Caucasian CF chromosomes, it has not been found on three normal chromosomes with the same ten site haplotype or twenty-four other normal Caucasian chromosomes. In six out of seven Caucasian patients who were found to have this mutation, it was paired with the $\Delta F_{508}$ mutation.

Figure 2:
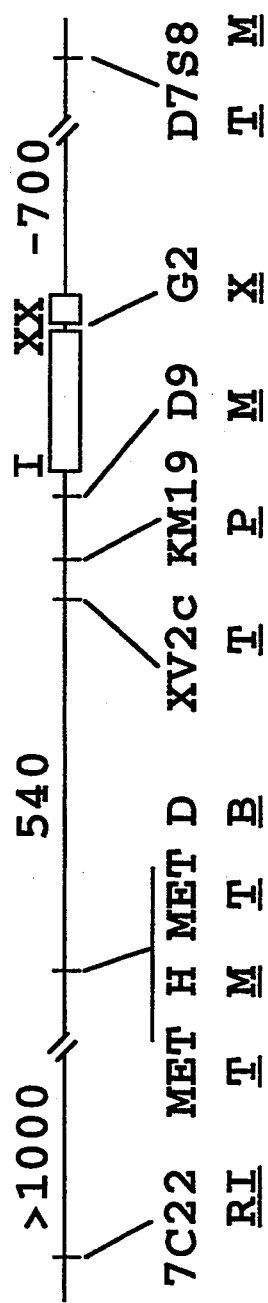
FIG. 2 shows a map of the relative positions and approximate distances in kb between the markers 7C22, MET, XV2c, KM19, D9, G2 and D7S8 and the CF gene which 4s shown as a box (Kerem, et al., *Science*, (1989) vol. 245, p. 1073; Estivill, et al., *Am. J. Hum. Genet.* (1989), vol. 44, p. 70 and Ramsay, et al., *Genomics* (1990), vol. 6, p. 39). Roman numerals denote exons 1 and 20 respectively. Enzyme abbreviations are as indicated in legend to Table 3.

The CF gene was identified solely by its location in the human genome (Rommens, et al., Science, vol. 245, p. 1059 (1989)). Little is known of the function of its protein product, CFTR, except by analogy to well-characterized proteins that have similar amino acid sequences (Riordan, et al., Science, vol. 245, p. 1066 (1989)). The four mutations described here occur within a 13 amino acid segment (codons 548 to 560) (see SEQ ID NO: 2) of the putative first NBF region in the CFTR protein which is highly conserved among similar regions of other membrane-associated transport proteins (Riordan, et al., Science, vol. 245, p. 1066 (1989)). Five amino acids in this region are completely conserved in comparable regions from the multiple drug resistance proteins indicating that these positions are probably crucial to protein function (FIG. 2). It appears to be significant that the amino acid substitutions described in this study occur at three of the five completely conserved residues. Moreover, the substitutions occur at the three most conserved residues in that region between CFTR and 14 other membrane associated proteins which bind ATP (Riordan, et al. Science (1989), vol. 245, p. 1066). Therefore, the location of these mutations supports the theory that the CFTR protein is a member of the ATP-dependent transport protein superfamily (Riordan, et al., Science, vol. 245, p. 1066 (1989); Higgins, Nature, vol. 341, p. 103 (1989)).

Nucleic acid probes are provided according to the present invention which comprise either ribonucleic or deoxyribonucleic acids. Typically, the size of the probes varies from approximately 18 to 22 nucleotides. Functionally, the probe is long enough to bind specifically to the homologous region of the CFTR gene, but short enough such that a difference of one nucleotide between the probe and the D N A being tested disrupts hybridization. Thus the nucleic acid probes of the present invention are capable of detecting single nucleotide changes in the CFTR gene. The probes of the present invention are complementary to the mutant alleles described here: $Asn_{549}$, $Asp_{551}$, $Stop_{553}$, $Thr_{559}$. The homology of the probes to the mutant alleles is 100%. Probes corresponding to the wild-type sequences in this, region of the CFTR gene can also be used. These probes will bind to wild-type sequences but not mutant alleles in the region of nucleotides 1776–1807. Thus, for example, one could determine whether an individual was homozygous or heterozygous for a particular allele using both a wild-type and an allele-specific probe. If no wild-type allele is present in an individual carrying one of these mutant alleles, the individual will be affected by cystic fibrosis.

The DNA samples of humans to be tested according to the present invention include DNA of fetuses, juveniles, and adults. The DNA can be directly analyzed upon removal from the human source, or the DNA may be amplified by the PCR technique (Saiki, et al., Science, vol. 230, p. 1350 (1985)). The PCR technique amplifies certain regions of the DNA selectively according to the primers which are used. Alternatively, cells may be isolated from the human source and grown in culture prior to isolation of DNA. Growth in culture may be required where the number of cells available for DNA isolation is limited. Amplification according the present invention is of exon 11 sequences. All or part of exon 11 may be amplified prior to testing in one of the methods of the present invention. Primers which may be used include the oligonucleotide primers 11i-5' (SEQ ID NO: 3) (5'-CAACTGTGGTTAAAG-CAATAGTGT-3') and 11i-3' (SEQ ID NO: 4) (5'-GCACAGATTCTGAGTAACCATAAT-3'). These primer sequences are selected from intron sequences flanking 5' and 3' of exon 11 of the CFTR gene. Other primers may be selected from known CFTR sequences which flank nucleotides 1778 to 1807.

According to one method of the present invention, mutations are detected by sequencing a region of exon 11 of the CFTR gene. The region includes nucleotides 1778 to 1807, which encompasses all four mutational sites taught herein. The sequences can be inspected by eye or by machine to determine if one of the mutations taught herein is present. These include an adenine at nucleotides nos. 1778, 1784, or 1807, or a thymidine residue at nucleotide no. 1789. Sequencing can be accomplished according to any means known in the art. Most simply this region of the genome can be amplified and then the sequence of the amplified region can be determined.

According to other methods of the present invention, the presence of the mutant alleles taught herein can be detected indirectly by testing for the loss or acquisition of specific restriction endonuclease sites. In particular, in the case of the $Asn_{549}$ allele, the mutation leads to a loss of a DdeI site (CTNAG) which can be detected using methods known in the art. Similarly, the $Asp_{551}$ allele carries a mutation which creates an MboI site (GATC) not present on the wild-type allele. Isoschizomers of DdeI and MboI can also be used. Both the Asp$_{551}$ and the Stop$_{553}$ alleles carry mutations which destroy a Hinc II site (GTYRN). In addition, any other restriction enzyme having a recognition sequence including one of the nucleotides 1778, 1784, 1807 or 1789 may be used, provided that the mutation either creates or destroys the recognition site. Detection of the new or missing restrictions enzyme sites can be accomplished according to any means known in the art. For example, Southern gels of genomic DNA can be used. The genomic DNA is digested with the appropriate restriction endonuclease and separated on an electrophoretic gel matrix such as agarose or acrylamide, as is known in the art. DNA separated on the gel matrix can be then transferred to another solid support on which hybridization can occur. The transfer can be accomplished according to any means known in the art such as wicking or electroblotting. Transferred DNA can be detected by hybridization with a nucleic acid probe which spans nucleotides 1778, 1784, or 1789. The probe should extend far enough beyond nucleotides 1778, 1784, or 1789 such that it is able to hybridize to a piece of DNA which has one end at nucleotide 1778, 1784, or 1789. Further the probe preferably does not span additional sites for the restriction endonuclease being used; this simplifies the analysis but is not necessary. Alternatively, the genomic DNA can be amplified as described above and then tested for the size and number of fragments generated with DdeI, MboI, HincII or other restriction endonuclease which recognize a sequence which includes nucleotides 1778, 1784, or 1789. If enzymes are found which specifically recognize the sequences at nucleotide 1807, they may also be used to detect the Thr$_{559}$ mutant allele.

According to still other methods of the present invention rapid screening techniques are used to determine whether exon 11 of the CFTR gene carries any mutations. Such techniques can be followed by one of the techniques already described above which are specific for a particular allele or mutation. One such rapid screening technique involves the determination of the conformation of single strands of DNA which have been amplified from exon 11 sequences. The single strands are run in non-denaturing electrophoretic gels, such as are typically used for sequencing DNA. The mobility of single stranded DNA on such gels is sensitive to the conformation of the DNA fragments. The conformation of the single stranded DNA is dependent on its base sequence, alterations in even one base affecting the conformation. Thus the presence of one of the CF alleles described herein can be detected by amplifying exon 11 sequences, denaturing the duplex molecules, and separating them on the basis of their conformation on non-denaturing polyacrylamide gels. If mutant alleles are present, they will have a different mobility than wild-type sequences amplified with the same primers. Most conveniently, the amplified sequences will be radiolabeled to facilitate visualization on gels. This can be readily accomplished using labeled primers or a labeled nucleotide. For a general reference on this technique see Orira, et al., Genomics vol. 5, pp. 874-879 (1989).

According to another rapid screening technique of the present invention amplified fragments containing mutations are detected using denaturing gradient gel electrophoresis (DGGE). For a general reference on this technique see Sheffield, et al., Proc. Natl. Acad. Sci. vol. 86, pp. 232-236 (1989). Briefly, double stranded fragments which are generated by amplification (PCR) can be subjected to DGGE. "DGGE is a gel system that separates DNA fragments according to their melting properties. When a DNA fragment is electrophoresed through a linearly increasing gradient of denaturants, the fragment remains double stranded until it reaches the concentration of denaturants equivalent to a melting temperature ($t_m$) that causes the lower-temperature melting domains of the fragment to melt. At this point, the branching of the molecule caused by partial melting sharply decreases the mobility of the fragment in the gel. The lower-temperature melting domains of DNA fragments differing by as little as a single-base substitution will melt at slightly different denaturant concentrations because of differences in stacking interactions between adjacent bases in each DNA strand. These differences in melting cause two DNA fragments to begin slowing down at different levels in the gel, resulting in their separation from each other." Sheffield, et al., ibid. Use of a GC clamp as taught in Myers et al., Nucleic Acids Res. vol. 13, pp. 3111-3146 (1985) increases the sensitivity of detection of this method from about 40% to about 100%. If mismatches are present, which would be the case if the DNA sample amplified was heterozygous for an exon 11 CFTR allele, they will be visible on these DGGE gels. Double stranded fragments containing one wild-type strand and one mutant strand will have a different mobility on these gels than will double stranded fragments which contain two wild-type or two mutant strands, due to the different melting temperatures of these species. Thus, the melting temperature of fragments amplified from exon 11 can be determined by DGGE and can indicate whether a mutant allele is present.

The following examples are not intended to limit the scope of the invention, but to illustrate various aspects of the invention.

EXAMPLE 1

This example shows the association of certain haplotypes with the $\Delta F_{508}$ and unknown CFTR mutations.

Haplotypes for four DNA markers were determined on 155 Caucasian and 43 Black CF chromosomes using three markers 5' of the CF gene (XV2c, KMI9 and Mp69.9) and one within the gene (G2).

DNA markers XV2e and KM19 and their associated polymorphisms are described for these populations elsewhere (Cutting, et al., Am. J. Hum. Genet., vol. 44, p. 307 (1989)). Probes D9 (Mp6d.9) and G2, which detect MspI and XbaI polymorphism sites respectively, were obtained from Professor Robert Williamson (Estivill, et al., Am. J. Hum. Genet., vol. 44, p. 70 (1989); Ramsay, et al., Genomies, vol. 6, p. 39 (1990)). Direct detection of the $\Delta F_{508}$ mutation was performed by PCR amplification of genomic DNA using primers C16B and C16D followed by vacuum blotting of amplified DNA to nitrocellulose filters and hybridization with either oligo N (Normal sequence) or oligo F (deletion Phe$_{508}$ sequence) as previously described (Kerem, et al., Science, vol. 245, p. 1073 (1989)). The results are shown in Table I below. Parentheses indicate frequency, — indicates that a polymorphism was uninformative or unknown, 1 is the absence and 2 the presence of a restriction site.

TABLE 1

| Haplotype | XV2c TaqI | KM19 PstI | D9 MspI | G2 XbaI | Caucasian Unk | Caucasian $\Delta F_{508}$ | American Black Unk | American Black $\Delta F_{508}$ |
|---|---|---|---|---|---|---|---|---|
| A | 1 | 1 | 1 | 2 | 6 | 0 | 1 | 0 |
| B | 1 | 1 | 2 | 2 | 2 | 0 | 2 | 0 |
| C | 1 | 2 | 1 | 2 | 0 | 0 | 1 | 0 |
| D | 1 | 2 | 2 | 1 | 12 | 5 | 1 | 0 |
| E | 1 | 2 | 2 | 2 | 6 | 92 | 2 | 7 |
| F | 2 | 1 | 1 | 2 | 1 | 0 | 4 | 0 |
| G | 2 | 2 | 1 | 1 | 0 | 0 | 1 | 0 |
| H | 2 | 2 | 2 | 1 | 2 | 1 | 1 | 0 |
| I | 2 | 2 | 2 | 2 | 0 | 6 | 2 | 2 |
| — | — | — | — | — | 6 | 16 | 12 | 7 |
|   |   |   |   |   | 35(.23) | 120(.77) | 27(.63) | 16(.37) |

The $\Delta F_{508}$ mutation was almost exclusively associated with one haplotype (E in Table 1) and accounted for 77% of the mutations on CF chromosomes from our Caucasian patients, similar to other studies of North American Caucasians (Kerem, et al., Science, vol. 245, p. 1073 (1989); Lemna, et al., New. Engl. J. Med., vol. 322, p. 291 (1990)). In contrast, only 16 of 43 (37%) CF chromosomes from American Black patients had the $\Delta F_{508}$ mutation, confirming that racial admixture alone does not account for the incidence of CF in this group. Caucasian CF chromosomes without the $\Delta F_{508}$ mutation, i.e., unknown, occur on 6 haplotypes with 24 of 29 chromosomes having either an A, D or E haplotype (Table 1). Unknown CF mutations in the American Black patients are associated with a wider distribution of haplotypes than in Caucasians, two of which may be unique to American Black patients.

EXAMPLE 2

This example demonstrates how the four new CFTR mutations were found.

An initial panel of ten Caucasian CF patients having fourteen of the 35 unknown mutations shown in Table 1 representing each haplotype group was selected for nucleotide sequencing (Orkin, et al., Nature, vol. 296, p. 627 (1982).) All of eighteen American Black patients with twenty-seven unknown mutations were examined. Exon 11 was sequenced in these patients as part of a systematic study of regions believed to be functionally important in the CFTR protein.

Figure 1:
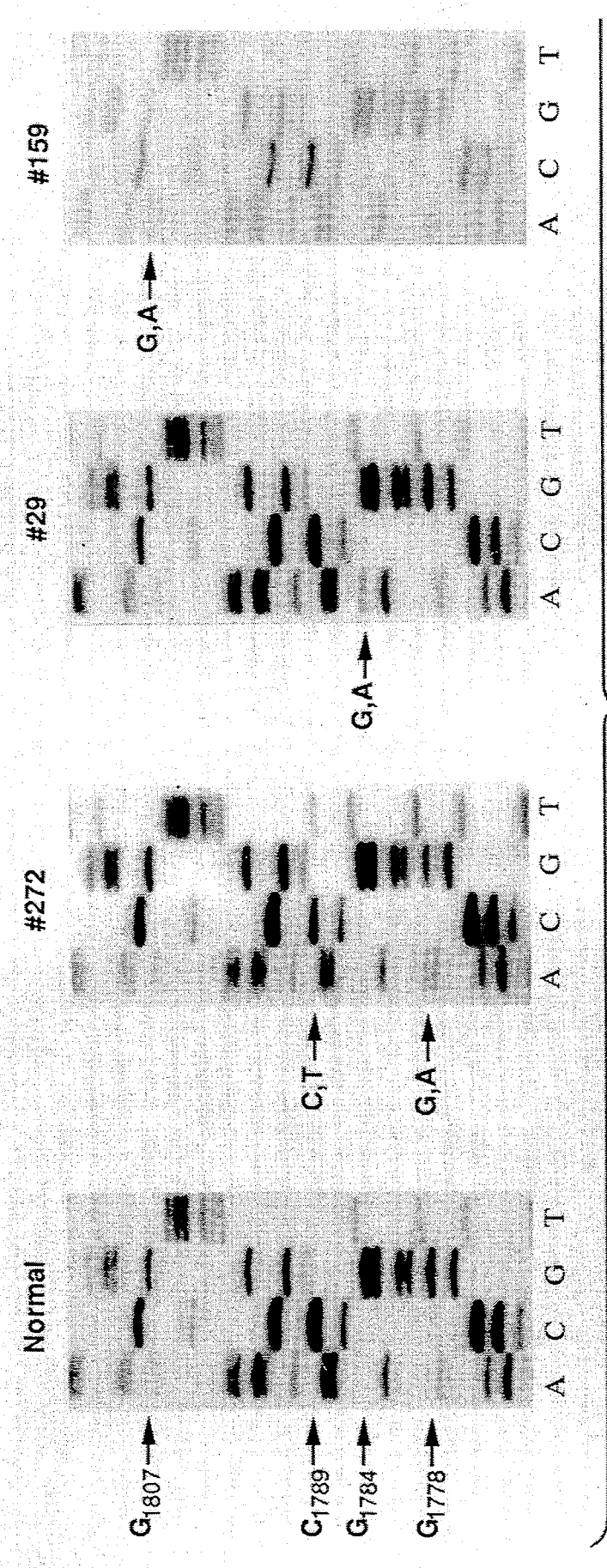
FIG. 1 shows direct sequence analysis of PCR amplified genomic DNA from exon 11 of CFTR using the primer 11i-5'. The order of nucleotides in each gel panel is A,C,G,T. Patient #272 has exon 11 mutations on each chromosome, $A_{1778}$ and $T_{1789}$. Patient #29 has the $A_{1784}$. Patient #159 has the $A_{1807}$ mutation.

Four mutations were detected in exon 11 of these patients, three cause amino acid substitutions, while the fourth produces a termination codon (FIG. 1). One mutation ($A_{1784}$) was found in 4% of our Caucasian CF chromosomes; the stop codon mutation ($T_{1789}$) occurred in 5% of our American Black CF chromosomes, while the remaining mutations ($A_{1807}$ and $A_{1778}$) are rare mutations in American Black patients (Table 2). The presence of each mutation has been confirmed in at least one relative of each patient.

TABLE 2

| Nucleotide | Amino Acid | Racial origin | CF Chromosome Haplotypes (# of Chromosomes)* |
|---|---|---|---|
| $G_{1778} \rightarrow A$ | $Ser_{549} \rightarrow Asn$ | American Black | A15(1) |
| $G_{1784} \rightarrow A$ | $Gly_{551} \rightarrow Asp$ | Caucasian | D16/18(5) D03(1) |
| $C_{1789} \rightarrow T$ | $Arg_{553} \rightarrow Stop$ | American Black | I12(1) Ii06(1) |
| $G_{1807} \rightarrow A$ | $Ala_{559} \rightarrow Thr$ | American Black | F(1) |

*Haplotype codes are created as follows: the first capitalized letter indicates the 4 site (XV2c, KM19, D9 and G2) haplotype shown in Table 1; numbers following the letter indicate the extended haplotype (7C22, MET, D7S8); i indicates an incomplete haplotype that is informative for at least three of the sites in the four site haplotype.

EXAMPLE 3

This example demonstrates how mutations $A_{1778}$ and $A_{1784}$ can be detected without sequencing.

PCR amplification of genomic DNA was performed as previously described (Saiki et al. Science, vol. 280, p. 1880 (1985)) using oligonucleotide primers 11i-5' (5'-CAACTGTGGTTAAAGCAATAGTGT-3') and 11i-3' (5'-GCACAGATTCTGAGTAACCATAAT-3') selected from intron sequences flanking 5' and 3' of exon 11 of the CFTR gene. Approximately 500 ng of genomic DNA extracted from peripheral lymphocytes of each subject was amplified using 2 microliters of a 10 micromolar solution of each primer described above in a total volume of 100 microliters containing 1X Taq Polymerase Buffer (50 mM KCl, mM Tris (pH 8.3), 1.5 mm MgCl₂, 0.01% (w/v) gelatin); 0.02 micromoles of each 2' deoxynucleotide 5' triphosphate (Pharmacia) and 2.5 units of Taq Polymerase (Cetus). Amplification was performed by 30 cycles of annealing at 58° for 30 seconds extension at 72° for 1 minute and denaturing at 94° for 30 seconds.

Amplification produced a 425 basepair fragment. Dde I digestion of DNA amplified from normal exon 11 sequence created two fragments of 174 and 251 bp whereas DNA amplified from exon 11 sequence containing the $A_{1778}$ mutation was not cut with Dde I. DNA amplified from normal exon 11 sequence (425 bp) cannot be cut with MboI whereas digestion of DNA amplified from exon 11 sequence containing the $A_{1784}$ mutation creates two fragments of 182 and 243 bp.

EXAMPLE 4

This example demonstrates that the three missense mutations are nor normal polymorphic variants of the CFTR gene.

In order to eliminate the possibility that the missense mutations are normal variants, non-CF chromosomes with the same haplotype as that associated with each particular mutation were analyzed by nucleotide sequencing or restriction digestion (Table 3).

TABLE 3

DNA polymorphism haplotypes associated with each exon 11 mutation

| Haplotype* | RI | T | M | T | B | T | P | M | X | T | M | CF Chromosomes** | Caucasian | Black | Normal Chromosomes*** | Caucasian | Black |
|---|---|---|---|---|---|---|---|---|---|---|---|---|---|---|---|---|---|
| Mutation $G_{1778} \rightarrow A$ | | | | | | | | | | | | $G_{1778} \rightarrow A$ | Normal at 1778 | | $G_{1778} \rightarrow A$ | Normal at 1778 | |
| A15 | 1 | 1 | 1 | 1 | 2 | 1 | 1 | 1 | 2 | 2 | 1 | 1 | 0 | 0 | 0 | 0 | 0 |
| A | — | — | — | — | — | 1 | 1 | 1 | 2 | — | — | 0 | 5**** | 0 | 0 | 32 | 6 |
| 1c | — | — | — | — | — | — | 1 | 1 | 2 | — | — | 0 | 1 | 4 | 0 | 0 | 29 |
| c | — | — | — | — | — | — | — | 1 | 2 | — | — | 0 | 0 | 3 | 0 | 8 | 18 |
| Other | — | — | — | — | — | — | — | — | — | — | — | 0 | 47 | 28 | 0 | 40 | 40 |
| | | | | | | | | | | | | 1 | 53 | 35 | 0 | 80 | 93 |
| Mutation $G_{1784} \rightarrow A$ | | | | | | | | | | | | $G_{1784} \rightarrow A$ | Normal at 1784 | | $G_{1784} \rightarrow A$ | Normal at 1784 | |
| D16/18 | 1 | 2 | 2 | 1 | 2 | 1 | 2 | 2 | 1 | 1 | — | 5 | 0 | 0 | 0 | 3 | 0 |
| D03 | 1 | 1 | 1 | 1 | 1 | 1 | 2 | 2 | 1 | 1 | — | 1 | 5 | 0 | 0 | 1 | 0 |
| D | — | — | — | — | — | 1 | 2 | 2 | 1 | — | — | 0 | 1 | 1 | 0 | 7 | 1 |
| Other | — | — | — | — | — | — | — | — | — | — | — | 0 | 42 | 35 | 0 | 16 | 35 |
| | | | | | | | | | | | | 6 | 48 | 36 | 0 | 27 | 36 |
| Mutation $C_{1789} \rightarrow A$ | | | | | | | | | | | | $C_{1789} \rightarrow A$ | Normal at 1789 | | $C_{1784} \rightarrow A$ | Normal at 1789 | |
| I12 | 1 | 1 | 1 | 1 | 2 | 2 | 2 | 2 | 2 | 2 | 1 | 1 | 0 | 0 | 0 | 0 | 0 |
| Ii06 | 1 | 1 | 1 | 1 | 2 | 2 | 2 | — | 2 | — | — | 1 | 0 | 0 | 0 | 0 | 0 |
| d | — | — | — | — | — | — | — | 2 | 2 | — | — | 0 | 6 | 7 | 0 | 0 | 0 |
| Other | — | — | — | — | — | — | — | — | — | — | — | 0 | 14 | 27 | 0 | 0 | 36 |
| | | | | | | | | | | | | 2 | 20 | 34 | 0 | 0 | 36 |
| Mutation $G_{1807} \rightarrow A$ | | | | | | | | | | | | $G_{1807} \rightarrow A$ | Normal at 1807 | | $G_{1807} \rightarrow A$ | Normal at 1807 | |
| F | — | — | — | — | — | 2 | 1 | 1 | 2 | — | — | 1 | 1 | 3 | 0 | 0 | 8 |
| Ic | — | — | — | — | — | — | 1 | 1 | 2 | — | — | 0 | 7 | 4 | 0 | 0 | 17 |
| c | — | — | — | — | — | — | — | 1 | 2 | — | — | 0 | 0 | 3 | 0 | 0 | 2 |
| Other | — | — | — | — | — | — | — | — | — | — | — | 0 | 12 | 25 | 0 | 0 | 9 |
| | | | | | | | | | | | | 1 | 20 | 35 | 0 | 0 | 36 |

Table 3 Legends
*Sites 7C22, MET and D7S8 have been previously described (Cutting, et al., Am. J. Hum. Genet. (1989), vol. 44, p. 307); 1 indicates the absence and 2 the presence of a particular site, — indicates that the site is different or uninformative. Enzyme abbreviations — RI(EcoRI), T(TaqI) M(MspI), B(BamI), P(PstI) and X(XbaI). The relative positions of the markers are indicated in FIG. 2.
**CF chromosomes include 21 Caucasian and 9 Black chromosomes with the $\Delta F_{508}$ mutation in the $G_{1778} \rightarrow A$ and $G_{1784} \rightarrow A$ group and 6 Caucasian and 9 Black chromosomes with the $\Delta F_{508}$ mutation in the $C_{1789} \rightarrow T$ and $G_{1807} \rightarrow A$ group. Twenty Caucasian CF and 36 Black CF chromosomes were directly sequenced in each case.
***Normal Caucasian chromosomes are from parents and/or siblings of CF patients and are therefore non-CF bearing. Normal Black chromosomes are either non-CF bearing chromosomes from healthy family members or chromosomes from Black patients heterozygous for sickle cell anemia or β-thalassemia (CF carrier frequency in American Blacks is 1 in 65 persons (Cutting, et al., Am. J. Hum. Genet. (1989), vol. 44, p. 307). Normal chromosomes with 4 site haplotypes (XV2c, KM19, Mp6d.9 and G2) identical to the mutation-bearing chromosomes were examined whenever possible. However, two or three site haplotypes, which included the intragenic marker G2 and the closest 5' markers (Mp6d.9± KM19), were also employed. Screening of normal chromosomes and additional Caucasian CF chromosomes for each mutation was as follows: PCR amplification of exon 11 followed by DdeI digestion to detect the $G_{1778} \rightarrow A$ mutation or MboI digestion to detect the $G_{1784} \rightarrow A$ mutation or direct sequencing to detect either the $C_{1789} \rightarrow T$ or $G_{1807} \rightarrow A$ mutations (Table 2).
****DNA from only five of the six Caucasian patients with an unknown mutation associated with haplotype A was available.

The $G_{1778} \rightarrow A$ ($Ser_{549} \rightarrow Asn$) mutation was identified on one chromosome from a Black CF patient and was inherited from the patient's mother. This mutation causes a conservative substitution between uncharged polar amino acids. To help confirm that this mutation is deleterious, normal chromosomes with the same haplotypes were analyzed. This mutation is associated with an eleven site haplotype (A15) seen only once in 198 (43 American Black, 155 Caucasian) chromosomes. However, the four site haplotype, composed of XV2C, KM19, D9 (Mp6d.9) and G2, designated A, is not rare in either race. This mutation could not be detected on 40 Caucasian or 53 American Black normal chromosomes with at least two sites in common with the haplotype (Table 3).

The $G_{1784} \rightarrow A$ ($Gly_{551} \rightarrow Asp$) mutation was discovered on six Caucasian chromosomes, five of which have the same ten site haplotype D16/18. The sixth occurred on a Chromosome which was identical at four sites closest to the gene (DO3 haplotype in Table 3) but which differed at the more distant sites. To date, this is the second most common CF mutation in Caucasians. It is unlikely that this mutation is a protein polymorphism since it replaces a neutral with a charged amino acid. Furthermore, the mutation occurs on 4% of Caucasian CF chromosomes in our sample and has not been found on 3 normal chromosomes with the same 10 site haplotype or 24 other normal Caucasian chromosomes. In 6 or 7 Caucasian patients (including two siblings) who were found to have this mutation, it was paired with the $\Delta F_{508}$ mutation. Three of these patients, ages 11 to 13 years, have mild lung disease with normal pulmonary function test results, while the other three patients, ages 15-17 years, have moderate to severe pulmonary disease. The seventh patient with the $Gly_{551} \rightarrow Asp$ mutation, age 31 years, has an unknown mutation on his other CF chromosome and manifests mild lung disease. All of the patients except one from the sibling pair have exocrine pancreatic insufficiency requiring pancreatic enzyme supplements. The range of illness severity and small number of patients precluded a meaningful assessment of the effect of this mutation on phenotype. All patients are of Northern European ancestry representing different ethnic groups.

The nucleotide substitution $C_{1789}$ to T ($Arg_{553} \rightarrow$ Stop) is the first nonsense mutation observed in the CFTR gene. It occurs at a CG dinucleotide, a "hotspot" for mutations, and it conforms to the CG→TG rule (Youssoufian, et al., Nature, vol. 324, p. 380 (1986); Soria, et al., Proc. Natl. Acad. Sci. USA, vol. 86, p. 587 (1989)). This mutation was found on two Black chromosomes having haplotypes identical at 8 informative sites (Table 3) suggesting a common origin of this mutation. It is unknown whether a stable truncated CFTR protein is present in vivo; however, in other disorders, nonsense mutations have been associated with unstable protein products (Adams, et al., Sem. Hematol., in press). Interestingly, one of the two patients with this nonsense mutation is a genetic compound with the $G_{1778} \rightarrow A$ ($Ser_{549} \rightarrow Asn$) mutation (Patient #272 in FIG. 1). This 13 year old patient has mild disease compared to patients homozygous for the $\Delta F_{508}$ mutation.

The fourth mutation, a $G_{1807}$ to A substitution was found on one chromosome from an American Black patient. This mutation causes a conservative change ($Ala_{559} \rightarrow Thr$) and since the remainder of the CF gene has not yet been sequenced, we were not convinced that this mutation is associated with disease. Fortunately, this mutation is associated with a relatively common four site haplotype (F) in the Black population. Direct sequencing of twenty-seven chromosomes with at least two sites in common with haplotype F from American Black sickle cell or $\beta$ thalassemia carriers did not reveal this mutation.

EXAMPLE 5

This example compares the sequence of CFTR in the region of the four disclosed mutations to other known proteins.

The four mutations described here occur within a thirteen amino acid segment (codons 548 to 560) of the first NBF region in the CFTR protein that is highly conserved with similar regions of other membrane-associated transport proteins (Riordan et al. Science vol. 245, pp. 1066–1073 (1989)). Five amino acids in this region are completely conserved in comparable regions from the multiple drug resistance proteins, indicating that these positions are probably crucial to protein function. It appears significant that the amino acid substitutions described in this study occur at three of the five completely conserved residues. Moreover, the substitutions occur at the three most conserved residues in that region between CFTR and fourteen other membrane associated proteins which bind A TP (shown in Riordan). The location of these mutations suggests that the CFTR protein is a member of the ATP-dependent transport protein superfamily (Riordan, supra; and Higgins, Nature, 341:103 (1989)).

We claim:

1. A nucleic acid probe which is complementary to a mutant allele of the CFTR gene said allele being selected from the group consisting of:
   $Asn_{549}$, $Asp_{551}$, $Stop_{553}$, and $Thr_{559}$.

2. The probe of claim 1 which is complementary to the $Asn_{549}$ allele.

3. The probe of claim 1 which is complementary to the $Thr_{559}$ allele.

4. The probe of claim 1 which is complementary to the $ASP_{551}$ allele.

5. The probe of claim 1 which is complementary to the $Stop_{553}$ allele.

6. A method of testing a DNA sample of a human to determine if the human is a carder of Cystic Fibrosis or if the human is affected with Cystic Fibrosis, comprising:
   providing a sample of DNA from a human;
   testing the sample for the presence of a mutation in exon 11 of the CFTR gene, said mutation comprising a nucleotide selected from the group consisting of: an adenine at nucleotide number 1778, 1784, or 1807, and a thymidine at nucleotide 1789, the presence of the mutation indicating that the human is a carder of Cystic Fibrosis or is affected with Cystic Fibrosis.

7. The method of claim 6 wherein the step of testing comprises amplifying exon 11 of said gene in a sample of DNA from the human to form a population of amplified DNA.

8. The method of claim 7 further comprising the step determining the conformation of single strands of the amplified DNA, a conformation different from that of single strands of amplified exon 11 of wild-type CFTR allele indicating an exon 11 mutation.

9. The method of claim 7 wherein the step of amplifying is performed in the presence of radiolabeled deoxynucleotide triphosphates or radiolabeled primers to form labeled amplified DNA.

10. The method of claim 8 wherein the conformation is determined by electrophoresis on non-denaturing gels.

11. The method of claim 7 further comprising the step of;
    determining the melting temperature of double strands of the amplified DNA, the presence of species of amplified DNA in the population of amplified DNA having different melting temperatures from DNA amplified from exon 11 of wild-type CFTR allele indicating a mutation in exon 11 of at least one allele of the CFTR gene in the human.

12. The method of claim 11 wherein the melting temperatures are determined by means of denaturing gradient gel electrophoresis.

13. The method of claim 6 further comprising:
    contacting the human DNA sample with a nucleic acid probe complementary to a mutant allele of the CFTR gene, said allele being selected from the group consisting of: $Asn_{549}$, $Asp_{551}$, $Stop_{553}$, and $Thr_{559}$, under conditions where totally homologous sequences anneal but sequences differing in one nucleotide do not;
    detecting whether the human DNA sample anneals to one of said probes, annealing to one of said probes indicating the presence of a mutant CFTR allele which can cause cystic fibrosis if no wild type allele is present in the human.

14. The method of claim 13 wherein the human DNA sample has been amplified to increase the number of copies of exon 11 of the CFTR gene.

15. The method of claim 6 further comprising:
    determining the nucleotide sequence of a region of exon 11 of a CFTR allele of a human, said region comprising nucleotides 1778–1807;
    inspecting the sequence to determine if there is an adenine at nucleotides number 1778, 1784, or 1807, or a thymidine at nucleotide number 1789, the presence of at least one of said nucleotides indicating a mutation in a CFTR allele which can cause cystic fibrosis if no wild-type CFTR allele is present in the human.

16. The method of claim 7 further comprising:
    digesting an aliquot of the amplified exon 11 DNA with a restriction endonuclease which recognizes a sequence CTNAG which occurs at nucleotide 1778 of the wild-type CFTR allele, to form DNA fragments;
    measuring the size of the amplified exon 11 DNA and the DNA fragments, DNA fragments which are the same size as the amplified exon 11 DNA indicating a mutation in a CFTR allele which can cause cystic fibrosis if no wild-type CFTR allele is present in the human.

17. The method of claim 16 wherein the endonuclease is DdeI.

18. The method of claim 7 further comprising:
digesting an aliquot of the amplified exon 11 DNA with a restriction endonuclease which recognizes a sequence GTYRAC which occurs at nucleotide 1784 of the wild-type CFTR allele, to form DNA fragments;
measuring the size of the amplified exon 11 DNA and the DNA fragments, DNA fragments which are the same size as the amplified exon 11 DNA indicating a mutation in a CFTR allele which can cause cystic fibrosis if no wild-type CFTR allele is present in the human.

19. The method of claim 18 wherein the endonuclease is HincII.

20. The method of claim 7 further comprising:
digesting an aliquot of the amplified exon 11 DNA with a restriction endonuclease which recognizes a sequence GTYRAC which occurs at nucleotide 1789 of the wild-type CFTR allele to form DNA fragments;
measuring the size of the amplified exon 11 DNA and the DNA fragments, DNA fragments which are the same size as the amplified exon 11 DNA indicating a mutation in a CFTR allele which can cause cystic fibrosis if no wild-type CFTR allele is present in the human.

21. The method of claim 20 wherein the endonuelease is HineII.

22. The method of claim 7 further comprising:
digesting an aliquot of the amplified exon 11 DNA with a restriction endonuclease which recognizes a sequence GATC which occurs at nucleotide 1784 of a mutant CFTR allele but does nor recognize the sequence in a wild-type CFTR allele, to form DNA fragments;
measuring the size of the amplified exon 11 DNA and the DNA fragments, DNA fragments which are not the same size as the amplified exon 11 DNA indicating a mutation in a CFTR allele which can cause cystic fibrosis if no wild-type CFTR allele is present in the human.

23. The method of claim 22 wherein the endonuclease is MboI.

24. The method of claim 6 further comprising:
digesting DNA of the human with a restriction endonuclease which recognizes a sequence GATC which occurs at nucleotide 1784 of a mutant CFTR allele but not of a wild-type CFTR allele:
separating the digested DNA on a gel matrix;
hybridizing the separated, digested DNA with an exon 11 probe which spans nucleotides 1784 but does not span any other sequence which the endonuclease recognizes;
detecting the DNA which hybridizes to the probe, two hybridizing fragments indicating a mutation in a CFTR allele of the human which can cause cystic fibrosis if no wild-type CFTR allele is present in the human.

25. The method of claim 24 wherein the endonuclease is MboI.

26. The method of claim 6 further comprising:
digesting DNA of the human with a restriction endonuclease which recognizes a sequence CTNAG which occurs at nucleotide 1778 of the wild-type CFTR allele;
separating the digested DNA on a gel matrix;
hybridizing the separated, digested DNA with an exon 11 probe which spans nucleotide 1778 but does not span any other sequence which the endonuclease recognizes;
detecting the DNA which hybridizes to the probe, only one hybridizing fragment indicating a mutation in a CFTR gene of the human which can cause cystic fibrosis if no wild-type CFTR allele is present in the human.

27. The method of claim 26 wherein the endonuclease is DdeI.

28. The method of claim 6 further comprising:
digesting DNA of the human with a restriction endonuclease which recognizes a sequence GTYRAC which occurs at nucleotide 1784 of the wild-type CFTR allele;
separating the digested DNA on a gel matrix;
hybridizing the separated, digested DNA with an exon 11 probe which spans nucleotide 1784 but does not span any other sequence which the endonuclease recognizes;
detecting the DNA which hybridizes to the probe, only one hybridizing fragment indicating a mutation in a CFTR gene of the human which can cause cystic fibrosis if no wild-type CFTR allele is present in the human.

29. The method of claim 28 wherein the endonuclease is HincII.

30. The method of claim 6 further comprising:
digesting DNA of the human with a restriction endonuclease which recognizes a sequence GTYRAC which occurs at nucleotide 1789 of the wild-type CFTR allele;
separating the digested DNA on a gel matrix;
hybridizing the separated, digested DNA with an exon 11 probe which spans nucleotide 1789 but does not span any other sequence which the endonuclease recognizes;
detecting the DNA which hybridizes to the probe, only one hybridizing fragment indicating a mutation in a CFTR gene of the human which can cause cystic fibrosis if no wild-type CFTR allele is present in the human.

31. The method of claim 30 wherein the endonuclease is HincII.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 6129 base pairs
( B ) TYPE: nucleic acid ( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:1:

| | | | | | | |
|---|---|---|---|---|---|---|
| AATTGGAAGC | AAATGACATC | ACAGCAGGTC | AGAGAAAAAG | GGTTGAGCGG | CAGGCACCCA | 60 |
| GAGTAGTAGG | TCTTTGGCAT | TAGGAGCTTG | AGCCCAGACG | GCCCTAGCAG | GGACCCCAGC | 120 |
| GCCCGAGAGA | CCATGCAGAG | GTCGCCTCTG | GAAAAGGCCA | GCGTTGTCTC | CAAACTTTTT | 180 |
| TTCAGCTGGA | CCAGACCAAT | TTTGAGGAAA | GGATACAGAC | AGCGCCTGGA | ATTGTCAGAC | 240 |
| ATATACCAAA | TCCCTTCTGT | TGATTCTGCT | GACAATCTAT | CTGAAAAATT | GGAAAGAGAA | 300 |
| TGGGATAGAG | AGCTGGCTTC | AAAGAAAAAT | CCTAAACTCA | TTAATGCCCT | TCGGCGATGT | 360 |
| TTTTTCTGGA | GATTTATGTT | CTATGGAATC | TTTTTATATT | TAGGGGAAGT | CACCAAAGCA | 420 |
| GTACAGCCTC | TCTTACTGGG | AAGAATCATA | GCTTCCTATG | ACCCGGATAA | CAAGGAGGAA | 480 |
| CGCTCTATCG | CGATTTATCT | AGGCATAGGC | TTATGCCTTC | TCTTTATTGT | GAGGACACTG | 540 |
| CTCCTACACC | CAGCCATTTT | TGGCCTTCAT | CACATTGGAA | TGCAGATGAG | AATAGCTATG | 600 |
| TTTAGTTTGA | TTTATAAGAA | GACTTTAAAG | CTGTCAAGCC | GTGTTCTAGA | TAAAATAAGT | 660 |
| ATTGGACAAC | TTGTTAGTCT | CCTTTCCAAC | AACCTGAACA | AATTTGATGA | AGGACTTGCA | 720 |
| TTGGCACATT | TCGTGTGGAT | CGCTCCTTTG | CAAGTGGCAC | TCCTCATGGG | CTAATCTGG | 780 |
| GAGTTGTTAC | AGGCGTCTGC | CTTCTGTGGA | CTTGGTTTCC | TGATAGTCCT | TGCCCTTTTT | 840 |
| CAGGCTGGGC | TAGGGAGAAT | GATGATGAAG | TACAGAGATC | AGAGAGCTGG | GAAGATCAGT | 900 |
| GAAAGACTTG | TGATTACCTC | AGAAATGATT | GAAAATATCC | AATCTGTTAA | GGCATACTGC | 960 |
| TGGAAGAAG | CAATGGAAAA | AATGATTGAA | AACTTAAGAC | AAACAGAACT | GAAACTGACT | 1020 |
| CGGAAGGCAG | CCTATGTGAG | ATACTTCAAT | AGCTCAGCCT | TCTTCTTCTC | AGGGTTCTTT | 1080 |
| GTGGTGTTTT | TATCTGTGCT | TCCCTATGCA | CTAATCAAAG | GAATCATCCT | CCGGAAAATA | 1140 |
| TTCACCACCA | TCTCATTCTG | CATTGTTCTG | CGCATGGCGG | TCACTCGGCA | ATTTCCCTGG | 1200 |
| GCTGTACAAA | CATGGTATGA | CTCTCTTGGA | GCAATAAACA | AATACAGGA | TTTCTTACAA | 1260 |
| AAGCAAGAAT | ATAAGACATT | GGAATATAAC | TTAACGACTA | CAGAAGTAGT | GATGGAGAAT | 1320 |
| GTAACAGCCT | TCTGGGAGGA | GGGATTTGGG | GAATTATTTG | AGAAAGCAAA | ACAAAACAAT | 1380 |
| AACAATAGAA | AAACTTCTAA | TGGTGATGAC | AGCCTCTTCT | TCAGTAATTT | CTCACTTCTT | 1440 |
| GGTACTCCTG | TCCTGAAAGA | TATTAATTTC | AAGATAGAAA | GAGGACAGTT | GTTGGCGGTT | 1500 |
| GCTGGATCCA | CTGGAGCAGG | CAAGACTTCA | CTTCTAATGA | TGATTATGGG | AGAACTGGAG | 1560 |
| CCTTCAGAGG | GTAAAATTAA | GCACAGTGGA | AGAATTTCAT | TCTGTTCTCA | GTTTTCCTGG | 1620 |
| ATTATGCCTG | GCACCATTAA | AGAAAATATC | ATCTTTGGTG | TTTCCTATGA | TGAATATAGA | 1680 |
| TACAGAAGCG | TCATCAAAGC | ATGCCAACTA | GAAGAGGACA | TCTCCAAGTT | TGCAGAGAAA | 1740 |
| GACAATATAG | TTCTTGGAGA | AGGTGGAATC | ACACTGAGTG | GAGGTCAACG | AGCAAGAATT | 1800 |
| TCTTTAGCAA | GAGCAGTATA | CAAAGATGCT | GATTTGTATT | TATTAGACTC | TCCTTTTGGA | 1860 |
| TACCTAGATG | TTTTAACAGA | AAAAGAAATA | TTTGAAAGCT | GTGTCTGTAA | ACTGATGGCT | 1920 |
| AACAAAACTA | GGATTTTGGT | CACTTCTAAA | ATGGAACATT | TAAAGAAAGC | TGACAAAATA | 1980 |
| TTAATTTTGA | ATGAAGGTAG | CAGCTATTTT | TATGGGACAT | TTCAGAACTA | CCAAAATCTA | 2040 |

```
CAGCCAGACT TTAGCTCAAA ACTCATGGGA TGTGATTCTT TCGACCAATT TAGTGCAGAA    2100
AGAAGAAATT CAATCCTAAC TGAGACCTTA CACCGTTTCT CATTAGAAGG AGATGCTCCT    2160
GTCTCCTGGA CAGAAACAAA AAAACAATCT TTTAAACAGA CTGGAGAGTT TGGGGAAAAA    2220
AGGAAGAATT CTATTCTCAA TCCAATCAAC TCTATACGAA AATTTTCCAT TGTGCAAAAG    2280
ACTCCCTTAC AAATGAATGG CATCGAAGAG GATTCTGATG AGCCTTTAGA GAGAAGGCTG    2340
TCCTTAGTAC CAGATTCTGA GCAGGGAGAG GCGATACTGC CTCGCATCAG CGTGATCAGC    2400
ACTGGCCCCA CGCTTCAGGC ACGAAGGAGG CAGTCTGTCC TGAACCTGAT GACACACTCA    2460
GTTAACCAAG GTCAGAACAT TCACCGAAAG ACAACAGCAT CCACACGAAA AGTGTCACTG    2520
GCCCCTCAGG CAAACTTGAC TGAACTGGAT ATATATTCAA GAAGGTTATC TCAAGAAACT    2580
GGCTTGGAAA TAAGTGAAGA AATTAACGAA GAAGACTTAA AGGAGTGCCT TTTTGATGAT    2640
ATGGAGAGCA TACCAGCAGT GACTACATGG AACACATACC TTCGATATAT TACTGTCCAC    2700
AAGAGCTTAA TTTTTGTGCT AATTTGGTGC TTAGTAATTT TTCTGGCAGA GGTGGCTGCT    2760
TCTTTGGTTG TGCTGTGGCT CCTTGGAAAC ACTCCTCTTC AAGACAAAGG GAATAGTACT    2820
CATAGTAGAA ATAACAGCTA TGCAGTGATT ATCACCAGCA CCAGTTCGTA TTATGTGTTT    2880
TACATTTACG TGGGAGTAGC CGACACTTTG CTTGCTATGG GATTCTTCAG AGGTCTACCA    2940
CTGGTGCATA CTCTAATCAC AGTGTCGAAA ATTTTACACC ACAAAATGTT ACATTCTGTT    3000
CTTCAAGCAC CTATGTCAAC CCTCAACACG TTGAAAGCAG GTGGGATTCT AATAGATTC    3060
TCCAAAGATA TAGCAATTTT GGATGACCTT CTGCCTCTTA CCATATTTGA CTTCATCCAG    3120
TTGTTATTAA TTGTGATTGG AGCTATAGCA GTTGTCGCAG TTTTACAACC CTACATCTTT    3180
GTTGCAACAG TGCCAGTGAT AGTGGCTTTT ATTATGTTGA GAGCATATTT CCTCCAAACC    3240
TCACAGCAAC TCAAACAACT GGAATCTGAA GGCAGGAGTC CAATTTTCAC TCATCTTGTT    3300
ACAAGCTTAA AAGGACTATG GACACTTCGT GCCTTCGGAC GGCAGCCTTA CTTTGAAACT    3360
CTGTTCCACA AAGCTCTGAA TTTACATACT GCCAACTGGT TCTTGTACCT GTCAACACTG    3420
CGCTGGTTCC AAATGAGAAT AGAAATGATT TTTGTCATCT TCTTCATTGC TGTTACCTTC    3480
ATTTCCATTT TAACAACAGG AGAAGGAGAA GGAAGAGTTG GTATTATCCT GACTTTAGCC    3540
ATGAATATCA TGAGTACATT GCAGTGGGCT GTAAACTCCA GCATAGATGT GGATAGCTTG    3600
ATGCGATCTG TGAGCCGAGT CTTTAAGTTC ATTGACATGC AACAGAAGG TAAACCTACC    3660
AAGTCAACCA AACCATACAA GAATGGCCAA CTCTCGAAAG TTATGATTAT TGAGAATTCA    3720
CACGTGAAGA AAGATGACAT CTGGCCCTCA GGGGGCCAAA TGACTGTCAA AGATCTCACA    3780
GCAAAATACA CAGAAGGTGG AAATGCCATA TTAGAGAACA TTTCCTTCTC AATAAGTCCT    3840
GGCCAGAGGG TGGGCCTCTT GGGAAGAACT GGATCAGGGA AGAGTACTTT GTTATCAGCT    3900
TTTTTGAGAC TACTGAACAC TGAAGGAGAA ATCCAGATCG ATGGTGTGTC TTGGGATTCA    3960
ATAACTTTGC AACAGTGGAG GAAAGCCTTT GGAGTGATAC CACAGAAAGT ATTTATTTTT    4020
TCTGGAACAT TTAGAAAAAA CTTGGATCCC TATGAACAGT GGAGTGATCA AGAAATATGG    4080
AAAGTTGCAG ATGAGGTTGG GCTCAGATCT GTGATAGAAC AGTTTCCTGG GAAGCTTGAC    4140
TTTGTCCTTG TGGATGGGGG CTGTGTCCTA AGCCATGGCC ACAAGCAGTT GATGTGCTTG    4200
GCTAGATCTG TTCTCAGTAA GGCGAAGATC TTGCTGCTTG ATGAACCCAG TGCTCATTTG    4260
GATCCAGTAA CATACCAAAT AATTAGAAGA ACTCTAAAAC AAGCATTTGC TGATTGCACA    4320
GTAATTCTCT GTGAACACAG GATAGAAGCA ATGCTGGAAT GCCAACAATT TTTGGTCATA    4380
GAAGAGAACA AAGTGCGGCA GTACGATTCC ATCCAGAAAC TGCTGAACGA GAGGAGCCTC    4440
TTCCGGCAAG CCATCAGCCC CTCCGACAGG GTGAAGCTCT TCCCCACCG GAACTCAAGC    4500
```

-continued

```
AAGTGCAAGT CTAAGCCCCA GATTGCTGCT CTGAAAGAGG AGACAGAAGA GAGGTGCAA      4560

GATACAAGGC TTTAGAGAGC AGCATAAATG TTGACATGGG ACATTTGCTC ATGGAATTGG      4620

AGCTCGTGGG ACAGTCACCT CATGGAATTG GAGCTCGTGG AACAGTTACC TCTGCCTCAG      4680

AAAACAAGGA TGAATTAAGT TTTTTTTTAA AAAAGAAACA TTTGGTAAGG GGAATTGAGG      4740

ACACTGATAT GGGTCTTGAT AAATGGCTTC CTGGCAATAG TCAAATTGTG TGAAAGGTAC      4800

TTCAAATCCT TGAAGATTTA CCACTTGTGT TTTGCAAGCC AGATTTTCCT GAAAACCCTT      4860

GCCATGTGCT AGTAATTGGA AAGGCAGCTC TAAATGTCAA TCAGCCTAGT TGATCAGCTT      4920

ATTGTCTAGT GAAACTCGTT AATTTGTAGT GTTGGAGAAG AACTGAAATC ATACTTCTTA      4980

GGGTTATGAT TAAGTAATGA TAACTGGAAA CTTCAGCGGT TTATATAAGC TTGTATTCCT      5040

TTTTCTCTCC TCTCCCATG ATGTTTAGAA ACACAACTAT ATTGTTTGCT AAGCATTCCA       5100

ACTATCTCAT TTCCAAGCAA GTATTAGAAT ACCACAGGAA CCACAAGACT GCACATCAAA      5160

ATATGCCCCA TTCAACATCT AGTGAGCAGT CAGGAAAGAG AACTTCCAGA TCCTGGAAAT      5220

CAGGGTTAGT ATTGTCCAGG TCTACCAAAA ATCTCAATAT TCAGATAAT CACAATACAT       5280

CCCTTACCTG GGAAAGGGCT GTTATAATCT TTCACAGGGG ACAGGATGGT TCCCTTGATG      5340

AAGAAGTTGA TATGCCTTTT CCCAACTCCA GAAAGTGACA AGCTCACAGA CCTTTGAACT      5400

AGAGTTTAGC TGGAAAAGTA TGTTAGTGCA AATTGTCACA GGACAGCCCT TCTTTCCACA      5460

GAAGCTCCAG GTAGAGGGTG TGTAAGTAGA TAGGCCATGG GCACTGTGGG TAGACACACA      5520

TGAAGTCCAA GCATTTAGAT GTATAGGTTG ATGGTGGTAT GTTTCAGGC TAGATGTATG       5580

TACTTCATGC TGTCTACACT AAGAGAGAAT GAGAGACACA CTGAAGAAGC ACCAATCATG      5640

AATTAGTTTT ATATGCTTCT GTTTTATAAT TTTGTGAAGC AAAATTTTTT CTCTAGGAAA      5700

TATTTATTTT AATAATGTTT CAAACATATA TTACAATGCT GTATTTAAA AGAATGATTA       5760

TGAATTACAT TTGTATAAAA TAATTTTTAT ATTTGAAATA TTGACTTTTT ATGGCACTAG      5820

TATTTTATG AAATATTATG TTAAAACTGG GACAGGGGAG AACCTAGGGT GATATTAACC       5880

AGGGGCCATG AATCACCTTT TGGTCTGGAG GGAAGCCTTG GGGCTGATCG AGTTGTTGCC      5940

CACAGCTGTA TGATTCCCAG CCAGACACAG CCTCTTAGAT GCAGTTCTGA AGAAGATGGT      6000

ACCACCAGTC TGACTGTTTC CATCAAGGGT ACACTGCCTT CTCAACTCCA AACTGACTCT      6060

TAAGAAGACT GCATTATATT TATTACTGTA AGAAAATATC ACTTGTCAAT AAAATCCATA      6120

CATTTGTGT                                                              6129
```

( 2 ) INFORMATION FOR SEQ ID NO:2:

( i ) SEQUENCE CHARACTERISTICS:
        ( A ) LENGTH: 1480 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: HOMO SAPIENS ( x i ) SEQUENCE DESCRIPTION: SEQ ID NO:2:

```
Met Gln Arg Ser Pro Leu Glu Lys Ala Ser Val Val Ser Lys Leu Phe
 1               5                  10                  15

Phe Ser Trp Thr Arg Pro Ile Leu Arg Lys Gly Tyr Arg Gln Arg Leu
                20                  25                  30

Glu Leu Ser Asp Ile Tyr Gln Ile Pro Ser Val Asp Ser Ala Asp Asn
             35                  40                  45

Leu Ser Glu Lys Leu Glu Arg Glu Trp Asp Arg Glu Leu Ala Ser Lys
         50                  55                  60
```

```
Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
                100                 105                 110

Asn Lys Glu Glu Arg Ser Ile Ala Ile Tyr Leu Gly Ile Gly Leu Cys
            115                 120                 125

Leu Leu Phe Ile Val Arg Thr Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
            195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
            485                 490                 495
```

```
Ile  Met  Pro  Gly  Thr  Ile  Lys  Glu  Asn  Ile  Ile  Phe  Gly  Val  Ser  Tyr
               500                 505                      510

Asp  Glu  Tyr  Arg  Tyr  Arg  Ser  Val  Ile  Lys  Ala  Cys  Gln  Leu  Glu  Glu
               515                 520                      525

Asp  Ile  Ser  Lys  Phe  Ala  Glu  Lys  Asp  Asn  Ile  Val  Leu  Gly  Glu  Gly
          530                 535                 540

Gly  Ile  Thr  Leu  Ser  Gly  Gln  Arg  Ala  Arg  Ile  Ser  Leu  Ala  Arg
545                      550                 555                           560

Ala  Val  Tyr  Lys  Asp  Ala  Asp  Leu  Tyr  Leu  Leu  Asp  Ser  Pro  Phe  Gly
               565                 570                      575

Tyr  Leu  Asp  Val  Leu  Thr  Glu  Lys  Glu  Ile  Phe  Glu  Ser  Cys  Val  Cys
               580                 585                      590

Lys  Leu  Met  Ala  Asn  Lys  Thr  Arg  Ile  Leu  Val  Thr  Ser  Lys  Met  Glu
          595                      600                 605

His  Leu  Lys  Lys  Ala  Asp  Lys  Ile  Leu  Ile  Leu  Asn  Glu  Gly  Ser  Ser
          610                 615                 620

Tyr  Phe  Tyr  Gly  Thr  Phe  Ser  Glu  Leu  Gln  Asn  Leu  Gln  Pro  Asp  Phe
625                      630                 635                           640

Ser  Ser  Lys  Leu  Met  Gly  Cys  Asp  Ser  Phe  Asp  Gln  Phe  Ser  Ala  Glu
               645                 650                      655

Arg  Arg  Asn  Ser  Ile  Leu  Thr  Glu  Thr  Leu  His  Arg  Phe  Ser  Leu  Glu
               660                 665                      670

Gly  Asp  Ala  Pro  Val  Ser  Trp  Thr  Glu  Thr  Lys  Lys  Gln  Ser  Phe  Lys
               675                 680                      685

Gln  Thr  Gly  Glu  Phe  Gly  Glu  Lys  Arg  Lys  Asn  Ser  Ile  Leu  Asn  Pro
     690                      695                 700

Ile  Asn  Ser  Ile  Arg  Lys  Phe  Ser  Ile  Val  Gln  Lys  Thr  Pro  Leu  Gln
705                      710                 715                           720

Met  Asn  Gly  Ile  Glu  Glu  Asp  Ser  Asp  Glu  Pro  Leu  Glu  Arg  Arg  Leu
               725                 730                      735

Ser  Leu  Val  Pro  Asp  Ser  Glu  Gln  Gly  Glu  Ala  Ile  Leu  Pro  Arg  Ile
               740                 745                      750

Ser  Val  Ile  Ser  Thr  Gly  Pro  Thr  Leu  Gln  Ala  Arg  Arg  Arg  Gln  Ser
          755                      760                 765

Val  Leu  Asn  Leu  Met  Thr  His  Ser  Val  Asn  Gln  Gly  Gln  Asn  Ile  His
770                      775                 780

Arg  Lys  Thr  Thr  Ala  Ser  Thr  Arg  Lys  Val  Ser  Leu  Ala  Pro  Gln  Ala
785                      790                 795                           800

Asn  Leu  Thr  Glu  Leu  Asp  Ile  Tyr  Ser  Arg  Arg  Leu  Ser  Gln  Glu  Thr
               805                 810                      815

Gly  Leu  Glu  Ile  Ser  Glu  Glu  Ile  Asn  Glu  Glu  Asp  Leu  Lys  Glu  Cys
               820                 825                      830

Leu  Phe  Asp  Asp  Met  Glu  Ser  Ile  Pro  Ala  Val  Thr  Thr  Trp  Asn  Thr
          835                 840                 845

Tyr  Leu  Arg  Tyr  Ile  Thr  Val  His  Lys  Ser  Leu  Ile  Phe  Val  Leu  Ile
     850                      855                 860

Trp  Cys  Leu  Val  Ile  Phe  Leu  Ala  Glu  Val  Ala  Ala  Ser  Leu  Val  Val
865                      870                 875                           880

Leu  Trp  Leu  Leu  Gly  Asn  Thr  Pro  Leu  Gln  Asp  Lys  Gly  Asn  Ser  Thr
               885                 890                      895

His  Ser  Arg  Asn  Asn  Ser  Tyr  Ala  Val  Ile  Ile  Thr  Ser  Thr  Ser  Ser
               900                 905                      910

Tyr  Tyr  Val  Phe  Tyr  Ile  Tyr  Val  Gly  Val  Ala  Asp  Thr  Leu  Leu  Ala
               915                 920                      925

Met  Gly  Phe  Phe  Arg  Gly  Leu  Pro  Leu  Val  His  Thr  Leu  Ile  Thr  Val
```

|     |     |     |     |     |     |     |     |     |     |     |     |     |     |     |
| --- | --- | --- | --- | --- | --- | --- | --- | --- | --- | --- | --- | --- | --- | --- |
|     |     |     |     | 930 |     |     |     | 935 |     |     |     | 940 |     |     |
| Ser | Lys | Ile | Leu | His | His | Lys | Met | Leu | His | Ser | Val | Leu | Gln | Ala | Pro |
| 945 |     |     |     | 950 |     |     |     | 955 |     |     |     |     |     | 960 |
| Met | Ser | Thr | Leu | Asn | Thr | Leu | Lys | Ala | Gly | Gly | Ile | Leu | Asn | Arg | Phe |
|     |     |     |     | 965 |     |     |     | 970 |     |     |     |     |     | 975 |
| Ser | Lys | Asp | Ile | Ala | Ile | Leu | Asp | Asp | Leu | Leu | Pro | Leu | Thr | Ile | Phe |
|     |     |     | 980 |     |     |     |     | 985 |     |     |     | 990 |     |     |
| Asp | Phe | Ile | Gln | Leu | Leu | Leu | Ile | Val | Ile | Gly | Ala | Ile | Ala | Val | Val |
|     |     | 995 |     |     |     |     | 1000|     |     |     |     | 1005|     |     |
| Ala | Val | Leu | Gln | Pro | Tyr | Ile | Phe | Val | Ala | Thr | Val | Pro | Val | Ile | Val |
|     |     | 1010|     |     |     | 1015|     |     |     | 1020|     |     |     |     |
| Ala | Phe | Ile | Met | Leu | Arg | Ala | Tyr | Phe | Leu | Gln | Thr | Ser | Gln | Gln | Leu |
| 1025|     |     |     | 1030|     |     |     | 1035|     |     |     |     |     | 1040|
| Lys | Gln | Leu | Glu | Ser | Glu | Gly | Arg | Ser | Pro | Ile | Phe | Thr | His | Leu | Val |
|     |     |     |     | 1045|     |     |     | 1050|     |     |     | 1055|     |     |
| Thr | Ser | Leu | Lys | Gly | Leu | Trp | Thr | Leu | Arg | Ala | Phe | Gly | Arg | Gln | Pro |
|     |     |     |     | 1060|     |     |     | 1065|     |     |     | 1070|     |     |
| Tyr | Phe | Glu | Thr | Leu | Phe | His | Lys | Ala | Leu | Asn | Leu | His | Thr | Ala | Asn |
|     |     |     |     | 1075|     |     |     | 1080|     |     |     | 1085|     |     |
| Trp | Phe | Leu | Tyr | Leu | Ser | Thr | Leu | Arg | Trp | Phe | Gln | Met | Arg | Ile | Glu |
|     |     |     |     | 1090|     |     |     | 1095|     |     |     | 1100|     |     |
| Met | Ile | Phe | Val | Ile | Phe | Phe | Ile | Ala | Val | Thr | Phe | Ile | Ser | Ile | Leu |
| 1105|     |     |     |     |     | 1110|     |     |     | 1115|     |     |     | 1120|
| Thr | Thr | Gly | Glu | Gly | Glu | Gly | Arg | Val | Gly | Ile | Ile | Leu | Thr | Leu | Ala |
|     |     |     |     | 1125|     |     |     | 1130|     |     |     | 1135|     |     |
| Met | Asn | Ile | Met | Ser | Thr | Leu | Gln | Trp | Ala | Val | Asn | Ser | Ser | Ile | Asp |
|     |     |     |     | 1140|     |     |     | 1145|     |     |     | 1150|     |     |
| Val | Asp | Ser | Leu | Met | Arg | Ser | Val | Ser | Arg | Val | Phe | Lys | Phe | Ile | Asp |
|     |     |     |     | 1155|     |     |     | 1160|     |     |     | 1165|     |     |
| Met | Pro | Thr | Glu | Gly | Lys | Pro | Thr | Lys | Ser | Thr | Lys | Pro | Tyr | Lys | Asn |
|     |     |     |     | 1170|     |     |     | 1175|     |     |     | 1180|     |     |
| Gly | Gln | Leu | Ser | Lys | Val | Met | Ile | Ile | Glu | Asn | Ser | His | Val | Lys | Lys |
| 1185|     |     |     |     |     | 1190|     |     |     | 1195|     |     |     | 1200|
| Asp | Asp | Ile | Trp | Pro | Ser | Gly | Gly | Gln | Met | Thr | Val | Lys | Asp | Leu | Thr |
|     |     |     |     | 1205|     |     |     | 1210|     |     |     | 1215|     |     |
| Ala | Lys | Tyr | Thr | Glu | Gly | Gly | Asn | Ala | Ile | Leu | Glu | Asn | Ile | Ser | Phe |
|     |     |     |     | 1220|     |     |     | 1225|     |     |     | 1230|     |     |
| Ser | Ile | Ser | Pro | Gly | Gln | Arg | Val | Gly | Leu | Leu | Gly | Arg | Thr | Gly | Ser |
|     |     |     |     | 1235|     |     |     | 1240|     |     |     | 1245|     |     |
| Gly | Lys | Ser | Thr | Leu | Leu | Ser | Ala | Phe | Leu | Arg | Leu | Leu | Asn | Thr | Glu |
|     |     |     |     | 1250|     |     |     | 1255|     |     |     | 1260|     |     |
| Gly | Glu | Ile | Gln | Ile | Asp | Gly | Val | Ser | Trp | Asp | Ser | Ile | Thr | Leu | Gln |
| 1265|     |     |     |     |     | 1270|     |     |     | 1275|     |     |     | 1280|
| Gln | Trp | Arg | Lys | Ala | Phe | Gly | Val | Ile | Pro | Gln | Lys | Val | Phe | Ile | Phe |
|     |     |     |     | 1285|     |     |     | 1290|     |     |     | 1295|     |     |
| Ser | Gly | Thr | Phe | Arg | Lys | Asn | Leu | Asp | Pro | Tyr | Glu | Gln | Trp | Ser | Asp |
|     |     |     |     | 1300|     |     |     | 1305|     |     |     | 1310|     |     |
| Gln | Glu | Ile | Trp | Lys | Val | Ala | Asp | Glu | Val | Gly | Leu | Arg | Ser | Val | Ile |
|     |     |     |     | 1315|     |     |     | 1320|     |     |     | 1325|     |     |
| Glu | Gln | Phe | Pro | Gly | Lys | Leu | Asp | Phe | Val | Leu | Val | Asp | Gly | Gly | Cys |
|     |     |     |     | 1330|     |     |     | 1335|     |     |     | 1340|     |     |
| Val | Leu | Ser | His | Gly | His | Lys | Gln | Leu | Met | Cys | Leu | Ala | Arg | Ser | Val |
| 1345|     |     |     |     |     | 1350|     |     |     | 1355|     |     |     | 1360|
| Leu | Ser | Lys | Ala | Lys | Ile | Leu | Leu | Leu | Asp | Glu | Pro | Ser | Ala | His | Leu |
|     |     |     |     | 1365|     |     |     | 1370|     |     |     | 1375|     |     |

-continued

| | | | | | | | | | | | | | |
|---|---|---|---|---|---|---|---|---|---|---|---|---|---|
| Asp | Pro | Val | Thr | Tyr | Gln | Ile | Ile | Arg | Arg | Thr | Leu | Lys | Gln | Ala | Phe |
| | | | 1380 | | | | | 1385 | | | | | 1390 | | |
| Ala | Asp | Cys | Thr | Val | Ile | Leu | Cys | Glu | His | Arg | Ile | Glu | Ala | Met | Leu |
| | | | 1395 | | | | | 1400 | | | | | 1405 | | |
| Glu | Cys | Gln | Gln | Phe | Leu | Val | Ile | Glu | Glu | Asn | Lys | Val | Arg | Gln | Tyr |
| | | | 1410 | | | | | 1415 | | | | | 1420 | | |
| Asp | Ser | Ile | Gln | Lys | Leu | Leu | Asn | Glu | Arg | Ser | Leu | Phe | Arg | Gln | Ala |
| 1425 | | | | | | 1430 | | | | | 1435 | | | | 1440 |
| Ile | Ser | Pro | Ser | Asp | Arg | Val | Lys | Leu | Phe | Pro | His | Arg | Asn | Ser | Ser |
| | | | | 1445 | | | | | 1450 | | | | | 1455 | |
| Lys | Cys | Lys | Ser | Lys | Pro | Gln | Ile | Ala | Ala | Leu | Lys | Glu | Glu | Thr | Glu |
| | | | | 1460 | | | | | 1465 | | | | | 1470 | |
| Glu | Glu | Val | Gln | Asp | Thr | Arg | Leu | | | | | | | | |
| | | | 1475 | | | | 1480 | | | | | | | | |

( 2 ) INFORMATION FOR SEQ ID NO:3:

( i ) SEQUENCE CHARACTERISTICS:
      ( A ) LENGTH: 24 base pairs
      ( B ) TYPE: nucleic acid
      ( C ) STRANDEDNESS: double
      ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
      ( A ) ORGANISM: HOMO SAPIENS ( x i ) SEQUENCE DESCRIPTION: SEQ ID NO:3:

CAACTGTGGT TAAAGCAATA GTGT       24

( 2 ) INFORMATION FOR SEQ ID NO:4:

( i ) SEQUENCE CHARACTERISTICS:
      ( A ) LENGTH: 24 base pairs
      ( B ) TYPE: nucleic acid
      ( C ) STRANDEDNESS: double
      ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
      ( A ) ORGANISM: HOMO SAPIENS ( x i ) SEQUENCE DESCRIPTION: SEQ ID NO:4:

GCACAGATTC TGAGTAACCA TAAT       24

32. The probe of claim 1 which comprises 18 to 22 nucleotides.

33. The method of claim 13 wherein said nucleic acid probe comprises 18 to 22 nucleotides.

* * * * *

UNITED STATES PATENT AND TRADEMARK OFFICE
CERTIFICATE OF CORRECTION

PATENT NO. : 5,407,796
DATED : April 18, 1995
INVENTOR(S) : Garry R. Cutting, et. al.

It is certified that error appears in the above-indentified patent and that said Letters Patent is hereby corrected as shown below:

In claim 6, column 11, lines 55 and 65 please delete each occurrence of the word "carder" and insert therefor --carrier--.

Please move claims 1-31 which appear at column 11, line 41 to column 14, line 55 and insert them after the sequence listing at column 27.

Signed and Sealed this

Twelfth Day of September, 1995

Attest:

BRUCE LEHMAN

*Attesting Officer*     *Commissioner of Patents and Trademarks*